United States Patent
Venugopala et al.

(10) Patent No.: US 11,981,674 B1
(45) Date of Patent: *May 14, 2024

(54) 7-ISOPROPYL 1-ETHYL/METHYL 3-(SUBSTITUTED BENZOYL)-2-SUBSTITUTED INDOLIZINE-1,7-DICARBOXYLATES AS LARVICIDAL AGENTS

(71) Applicant: KING FAISAL UNIVERSITY, Al-Ahsa (SA)

(72) Inventors: Katharigatta N. Venugopala, Al-Ahsa (SA); Sandeep Chandrashekharappa, Lucknow (IN); Pran Kishore Deb, Ranchi (IN); Osama I. Alwassil, Al-Ahsa (SA); Rashmi Venugopala, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/500,084

(22) Filed: Nov. 1, 2023

(51) Int. Cl.
*C07D 471/04* (2006.01)
*A01N 43/90* (2006.01)
*A01P 7/04* (2006.01)

(52) U.S. Cl.
CPC .......... *C07D 471/04* (2013.01); *A01N 43/90* (2013.01); *A01P 7/04* (2021.08)

(58) Field of Classification Search
CPC .................................................... C07D 471/04
USPC ............................................................ 514/299
See application file for complete search history.

(56) References Cited

U.S. PATENT DOCUMENTS 11,807,640 B1 * 11/2023 Venugopala ......... C07D 471/04
2006/0049410 A1    3/2006 Hosokawa et al.

FOREIGN PATENT DOCUMENTS

KR    1020200124455    3/2020

OTHER PUBLICATIONS

Huang et al., Molecular Diversity (2013), 17(2), 221-243.*
Venugopala et al., "Novel Series of Methyl 3-(Substituted Benzoyl)-7-Substituted-2-Phenylindolizine-1-Carboxylates as Promising Anti-Inflammatory Agents: Molecular Modeling Studies", Biomolecules. Nov. 2019; 9(11): 661.
Shi et al., "Transition-Metal-Free Synthesis of Indolizines from Electron-DeficientAlkenesvia One-Pot Reaction Using TEMPO as an Oxidant", Synthesis 2016; 48(03): 413-420.

* cited by examiner

*Primary Examiner* — Niloofar Rahmani
(74) *Attorney, Agent, or Firm* — Nath, Goldberg & Meyer; Richard C. Litman

(57) ABSTRACT

Compounds for treating preventing malaria and, particularly, to larvicidal agents that are 7-isopropyl 1-ethyl/methyl 3-(substituted benzoyl)-2-substituted indolizine-1,7-dicarboxylates derivatives and their use as larvicidal agents.

17 Claims, No Drawings

7-ISOPROPYL 1-ETHYL/METHYL 3-(SUBSTITUTED BENZOYL)-2-SUBSTITUTED INDOLIZINE-1,7-DICARBOXYLATES AS LARVICIDAL AGENTS

BACKGROUND

1. Field

The present disclosure relates to the synthesis of 7-isopropyl 1-ethyl/methyl 3-(substituted benzoyl)-2-substituted indolizine-1,7-dicarboxylates as larvicidal agents and their use as larvicidal agents.

2. Description of the Related Art

Malaria is considered one of the most challenging life-threatening diseases initiated by parasites that are transmitted to humans through the bites of infected *Anopheles* mosquitoes. It affects both genders, leading to severe health impacts and negative socioeconomic impacts. Recently, the World Health Organization (WHO) reported that there were an estimated 228 million cases of malaria spanning 87 countries. The *Anopheles arabiensis* mosquito is considered one of the major vectors of malaria. The path of infection starts with a bite from an infected female mosquito, where the parasite is delivered into the circulatory system and ultimately to the liver, where it become mature and reproduces.

There are many approaches and strategies for the management of Malaria. One of the most effective strategies is to eliminate the vector through environmental modifications and biological control, The use of long-lasting insecticidal nets (LLINs) and indoor residual spraying (IRS) or safe synthetic larvicidal agents are candidates for biological control. Since insecticide resistance threatens the management of vectors, it is necessary to prioritize the development of potent new biologically active compounds as well as to aid in resistance management.

Thus, new insecticides and/or pesticides solving the aforementioned problems are desired.

SUMMARY

In the process of designing and developing a novel larvicidal agent, a series of 7-isopropyl 1-ethyl/methyl 3-(substituted benzoyl)-2-substituted indolizine-1,7-dicarboxylates derivatives have been developed by a one-step synthetic chemical method. The present subject matter relates to the synthesis of an anti-malarial drug designed to kill, for example, the mosquito vector *Anopheles arabiensis* at the larval stage. The compounds were evaluated for larvicidal activity, for example against *Anopheles arabiensis*, by standard WHO larvicidal protocols. Tested compounds resulted in high overall larval mortality of greater than 70% after 24 hours and 48 hours.

In an embodiment, the present subject matter relates to a compound having the formula I:

I 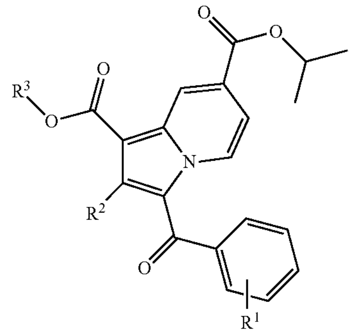 wherein:

$R^1$ is selected from the group consisting of H, $CH_3$, F, Cl, Br, 3,5-$CF_3$, and CN;

$R^2$ is selected from the group consisting of H, $COOCH_3$ and $COOC_2H_5$; and $R^3$ is selected from the group consisting of $CH_3$ and $C_2H_5$.

In a further embodiment, the present subject matter relates to a compound selected from the group consisting of: 7-isopropyl 1,2-dimethyl 3-benzoylindolizine-1,2,7-tricarboxylate (3a); 1-ethyl 7-isopropyl 3-benzoylindolizine-1,7-dicarboxylate (3b); 7-isopropyl 1,2-dimethyl 3-(4-fluorobenzoyl)indolizine-1,2,7-tricarboxylate (3c); 1-ethyl 7-isopropyl 3-(4-fluorobenzoyl)indolizine-1,7-dicarboxylate (3d); 7-isopropyl 1,2-dimethyl 3-(4-chlorobenzoyl)indolizine-1,2,7-tricarboxylate (3e); 1-ethyl 7-isopropyl 3-(4-chlorobenzoyl)indolizine-1,7-dicarboxylate (3f); 7-isopropyl 1,2-dimethyl 3-(4-bromobenzoyl)indolizine-1,2,7-tricarboxylate (3g); 1-ethyl 7-isopropyl 3-(4-bromobenzoyl)indolizine-1,7-dicarboxylate (3h); 7-isopropyl 1,2-dimethyl 3-(4-cyanobenzoyl)indolizine-1,2,7-tricarboxylate (3i); 1-ethyl 7-isopropyl 3-(4-cyanobenzoyl)indolizine-1,7-dicarboxylate (3j); 7-isopropyl 1,2-dimethyl 3-(4-methylbenzoyl)indolizine-1,2,7-tricarboxylate (3k); 7-isopropyl 1,2-dimethyl 3-(3,5-bis(trifluoromethyl)benzoyl)indolizine-1,2,7-tricarboxylate (3l); and 1-ethyl 7-isopropyl 3-(3,5-bis(trifluoromethyl)benzoyl)indolizine-1,7-dicarboxylate (3m).

In one embodiment, the present subject matter relates to a method of killing insects and larvae, the method comprising applying to the food of said insects and larvae in a target site of insect infestation a larvicidal effective amount of a larvicidal active composition comprising a compound of the formula I and an acceptable carrier:

I wherein:

R$^1$ is selected from the group consisting of H, CH$_3$, F, Cl, Br, 3,5-CF$_3$, and CN;

R$^2$ is selected from the group consisting of H, COOCH$_3$ and COOC$_2$H$_5$; and R$^3$ is selected from the group consisting of CH$_3$ and C$_2$H$_5$.

In various embodiments, R$^2$ may be COOCH$_3$, R$^3$ may be CH$_3$ and R$_1$ may be selected from the group consisting of H, CH$_3$, F, Cl, Br, 3,5-CF$_3$, and CN. In other embodiments, R$^2$ may be COOC$_2$H$_5$, R$^3$ may be C$_2$H$_5$ and R$_1$ may be selected from the group consisting of H, CH$_3$, F, Cl, Br, 3,5-CF$_3$, and CN. In additional embodiments, R$^2$ may be H, R$^3$ may be CH$_2$CH$_3$, and R$_1$ may be selected from the group consisting of H, F, Cl, Br, 3,5-CF$_3$, and CN.

In another embodiment, the present subject matter relates to the use of an insecticidally acceptable composition comprising an insecticidally effective amount of the compounds of formula I, including a number of species or specific structures falling under structural formula I.

In a further embodiment, the present subject matter relates to a method of killing insects comprising applying to food of the insects or to a target site of insect infestation an insecticidally effective amount of compounds of formula I.

These and other features of the present subject matter will become readily apparent upon further review of the following specifications.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C$_1$-C$_{40}$ alkyl group), for example, 1-30 carbon atoms (i.e., C$_1$-C$_{30}$ alkyl group). In some embodiments, an alkyl group can have 1 to 6 carbon atoms, and can be referred to as a "lower alkyl group" or a "C$_1$-C$_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

The term “isomers” or “stereoisomers” as used herein relates to compounds that have identical molecular formulae but that differ in the arrangement of their atoms in space. Stereoisomers that are not mirror images of one another are termed “diastereoisomers” and stereoisomers that are non-superimposable minor images are termed “enantiomers,” or sometimes optical isomers. A carbon atom bonded to four non-identical substituents is termed a “chiral center.” Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use “comprising” language. However, it will be understood by one of skill in the art, that in some specific instances, an embodiment can alternatively be described using the language “consisting essentially of” or “consisting of”.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term “about”. Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the synthesis of an anti-malarial drug designed to kill, for example, the mosquito vector *Anopheles arabiensis* at the larval stage. The compounds were evaluated for larvicidal activity, for example against *Anopheles arabiensis*, by standard WHO larvicidal protocols. Tested compounds resulted in high overall larval mortality of greater than 70% after 24 hours and 48 hours.

In an embodiment, the present subject matter relates to a compound having the formula I:

I 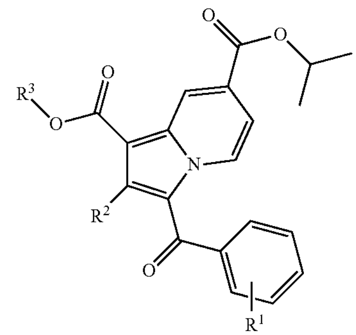 wherein:

$R^1$ may be selected from the group consisting of H, $CH_3$, F, Cl, Br, 3,5-$CF_3$, and CN;

$R^2$ may be selected from the group consisting of H, $COOCH_3$, and $COOC_2H_5$; and $R^3$ may be selected from the group consisting of $CH_3$ and $C_2H_5$.

In one embodiment, where $R^2$ is $COOCH_3$, and $R^3$ is $CH_3$, $R^1$ may be selected from the group consisting of H, $CH_3$, F, Cl, Br, 3,5-$CF_3$, and CN. Similarly, where $R^2$ is $COOC_2H_5$ and $R^3$ is $C_2H_5$, $R^1$ may be selected from the group consisting of H, $CH_3$, F, Cl, Br, 3,5-$CF_3$, and CN. In additional embodiments, $R^2$ may be H, $R^3$ may be $CH_2CH_3$, and $R_1$ may be selected from the group consisting of H, F, Cl, Br, 3,5-$CF_3$, and CN.

In certain embodiments, the compound can be selected from the group consisting of: 7-isopropyl 1,2-dimethyl 3-benzoylindolizine-1,2,7-tricarboxylate (3a); 1-ethyl 7-isopropyl 3-benzoylindolizine-1,7-dicarboxylate (3b); 7-isopropyl 1,2-dimethyl 3-(4-fluorobenzoyl)indolizine-1,2,7-tricarboxylate (3c); 1-ethyl 7-isopropyl 3-(4-fluorobenzoyl)indolizine-1,7-dicarboxylate (3d); 7-isopropyl 1,2-dimethyl 3-(4-chlorobenzoyl)indolizine-1,2,7-tricarboxylate (3e); 1-ethyl 7-isopropyl 3-(4-chlorobenzoyl)indolizine-1,7-dicarboxylate (3f); 7-isopropyl 1,2-dimethyl 3-(4-bromobenzoyl)indolizine-1,2,7-tricarboxylate (3g); 1-ethyl 7-isopropyl 3-(4-bromobenzoyl)indolizine-1,7-dicarboxylate (3h); 7-isopropyl 1,2-dimethyl 3-(4-cyanobenzoyl)indolizine-1,2,7-tricarboxylate (3i); 1-ethyl 7-isopropyl 3-(4-cyanobenzoyl)indolizine-1,7-dicarboxylate (3j); 7-isopropyl 1,2-dimethyl 3-(4-methylbenzoyl)indolizine-1,2,7-tricarboxylate (3k); 7-isopropyl 1,2-dimethyl 3-(3,5-bis(trifluoromethyl)benzoyl)indolizine-1,2,7-tricarboxylate (3l); and 1-ethyl 7-isopropyl 3-(3,5-bis(trifluoromethyl)benzoyl)indolizine-1,7-dicarboxylate (3m).

Said differently, the present subject matter can related to compounds of formula I, i.e. 7-isopropyl 1-ethyl/methyl 3-(substituted benzoyl)-2-substituted indolizine-1,7-dicarboxylates, selected from the group consisting of:

TABLE 1

| Sample code | Chemical Structure | IUPAC Nomenclature |
|---|---|---|
| 3a | 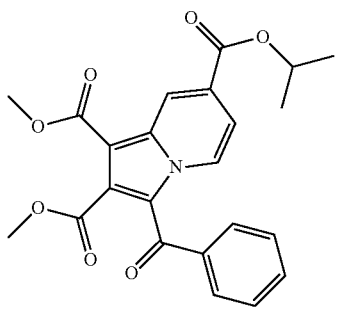 [SMILES: COC(=O)c1c(C(=O)OC)c2cc(C(=O)OC(C)C)ccn2c1C(=O)c1ccccc1] | 7-Isopropyl 1,2-dimethyl 3-benzoylindolizine-1,2,7-tricarboxylate |
| 3b | 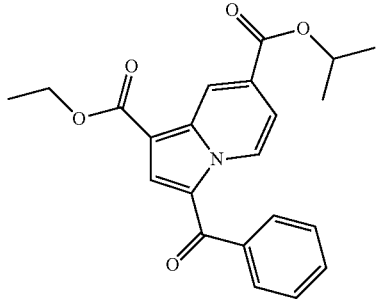 [SMILES: CCOC(=O)c1cc(C(=O)c2ccccc2)n2ccc(C(=O)OC(C)C)cc12] | 1-Ethyl 7-isopropyl 3-benzoylindolizine-1,7-dicarboxylate |
| 3c | 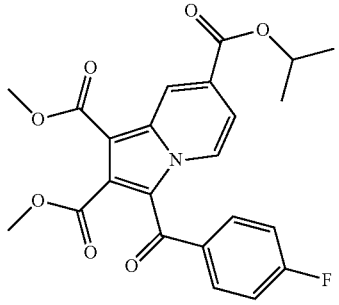 [SMILES: COC(=O)c1c(C(=O)OC)c2cc(C(=O)OC(C)C)ccn2c1C(=O)c1ccc(F)cc1] | 7-Isopropyl 1,2-dimethyl 3-(4-fluorobenzoyl)indolizine-1,2,7-tricarboxylate |
| 3d | 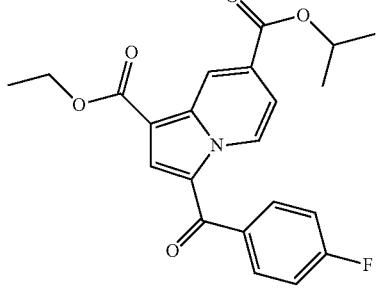 | 1-Ethyl 7-isopropyl 3-(4-fluorobenzoyl)indolizine-1,7-dicarboxylate |
| 3e | 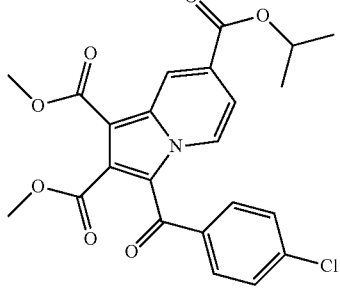 | 7-Isopropyl 1,2-dimethyl 3-(4-chlorobenzoyl)indolizine-1,2,7-tricarboxylate |

TABLE 1-continued

| Sample code | Chemical Structure | IUPAC Nomenclature |
| --- | --- | --- |
| 3f | 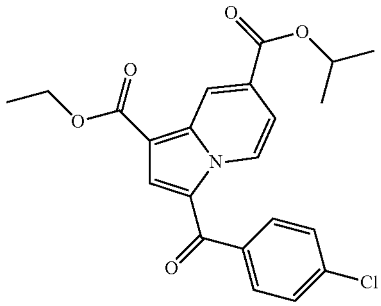 [SMILES: CCOC(=O)c1cc(C(=O)c2ccc(Cl)cc2)n2ccc(C(=O)OC(C)C)cc12] | 1-Ethyl 7-isopropyl 3-(4-chlorobenzoyl)indolizine-1,7-dicarboxylate |
| 3g | 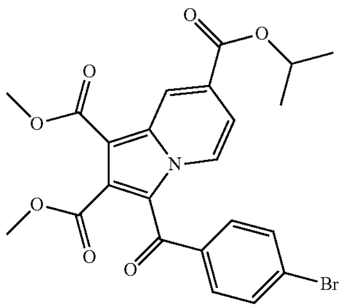 [SMILES: COC(=O)c1c(C(=O)OC)c2cc(C(=O)OC(C)C)ccn2c1C(=O)c1ccc(Br)cc1] | 7-Isopropyl 1,2-dimethyl 3-(4-bromobenzoyl)indolizine-1,2,7-tricarboxylate |
| 3h | 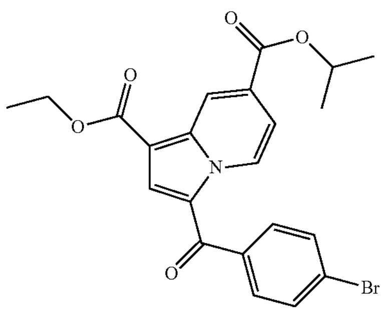 [SMILES: CCOC(=O)c1cc(C(=O)c2ccc(Br)cc2)n2ccc(C(=O)OC(C)C)cc12] | 1-Ethyl 7-isopropyl 3-(4-bromobenzoyl)indolizine-1,7-dicarboxylate |
| 3i | 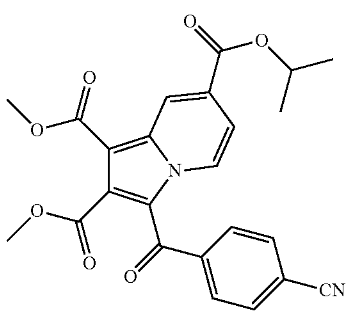 [SMILES: COC(=O)c1c(C(=O)OC)c2cc(C(=O)OC(C)C)ccn2c1C(=O)c1ccc(C#N)cc1] | 7-Isopropyl 1,2-dimethyl 3-(4-cyanobenzoyl)indolizine-1,2,7-tricarboxylate |
| 3j | 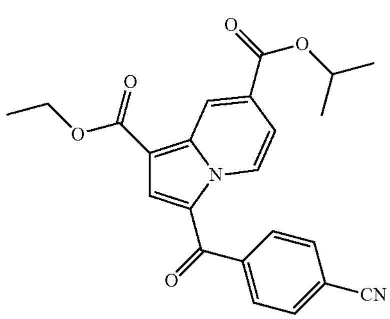 [SMILES: CCOC(=O)c1cc(C(=O)c2ccc(C#N)cc2)n2ccc(C(=O)OC(C)C)cc12] | 1-Ethyl 7-isopropyl 3-(4-cyanobenzoyl)indolizine-1,7-dicarboxylate |

TABLE 1-continued

| Sample code | Chemical Structure | IUPAC Nomenclature |
|---|---|---|
| 3k | 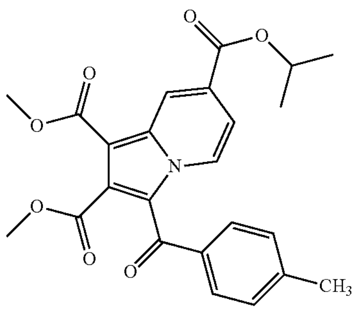 [SMILES: COC(=O)c1c(C(=O)OC)c2cc(C(=O)OC(C)C)ccn2c1C(=O)c1ccc(C)cc1] | 7-Isopropyl 1,2-dimethyl 3-(4-methylbenzoyl)indolizine-1,2,7-tricarboxylate |
| 3l | 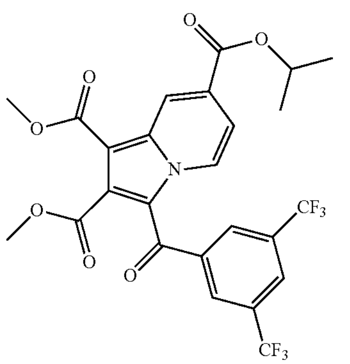 [SMILES: COC(=O)c1c(C(=O)OC)c2cc(C(=O)OC(C)C)ccn2c1C(=O)c1cc(C(F)(F)F)cc(C(F)(F)F)c1] | 7-Isopropyl 1,2-dimethyl 3-(3,5-bis(trifluoromethyl)benzoyl)indolizine-1,2,7-tricarboxylate |
| 3m | 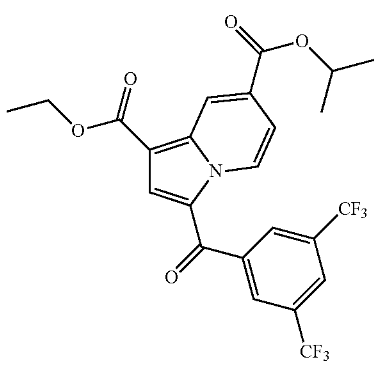 [SMILES: CCOC(=O)c1cc(C(=O)c2cc(C(F)(F)F)cc(C(F)(F)F)c2)n2ccc(C(=O)OC(C)C)cc12] | 1-Ethyl 7-isopropyl 3-(3,5-bis(trifluoromethyl)benzoyl)indolizine-1,7-dicarboxylate |

It is to be understood that the present subject matter covers all combinations of substituent groups referred to herein.

In additional embodiments, the compound of formula I is considered as larvicidal agent. Accordingly, the present compound is capable of killing the larval stage of an insect.

In another embodiment, the present subject matter relates to an insecticidally acceptable composition comprising an insecticidally effective amount of compound of formula I and an insecticidally acceptable carrier.

In some embodiments, the present compositions and methods of use can be used for combination treatment, where other insecticidal ingredients can be included therein, or can be co-administered therewith.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art.

The present compounds are typically administered at an insecticidally effective dosage, e.g., a dosage sufficient to provide a desired activity against insects.

While insecticidal dosage levels have yet to be optimized for the present compounds, generally, each treatment of the present compositions could be expected to include 1 mg/mL in 1 mL of a suitable carrier and 249 mL of water to obtain a final concentration of 4 μg/mL, of the present compounds. The precise effective amount will vary from treatment to treatment and will depend upon the target area of application, the insect species being treated for, the number of insects present, and the like. The treatment area may be administered in as many doses as is required to produce an effective treatment.

Liquid compositions can, for example, be prepared by dissolving, dispersing, etc. the active compound as defined above and optional adjuvants in a carrier, such as, for example, water, saline, aqueous dextrose, glycerol, glycols, ethanol, and the like, to thereby form a solution or suspension. If desired, the composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

In a further embodiment, the present subject matter relates to a method of killing insects and larvae comprising applying to said insects or to a target site of insect infestation an insecticidally effective amount of the compound of formula I and/or a composition containing the same.

In an embodiment, the present methods of killing insects can be effective against insects belonging to a species *Anopheles arabiensis* of mosquitos. Accordingly, the present compounds can be used as an insecticide to control populations of harmful insect pests, including, by way of non-limiting example, cockroaches and fleas.

In one embodiment, in the present methods of killing insects, the compounds as described herein can have a high larval mortality rate of 32.57±2.44 to 97.21±2.30 in 24 hours and 36.76±1.79 to 99.52±1.49 in 48 hours.

In another embodiment, in the present methods of killing insects, the compounds as described herein, as exemplified by the 7-isopropyl 1,2-dimethyl 3-benzoylindolizine-1,2,7-tricarboxylate (3a) compound, can have a high larval mortality rate of 39.19±1.64 in 24 hours and 45.53±2.65 in 48 hours.

In yet another embodiment, in the present methods of killing insects, the 1-ethyl 7-isopropyl 3-benzoylindolizine-1,7-dicarboxylate (3b) compound can have a high larval mortality rate of 32.57±2.44 in 24 hours and 36.76±1.79 in 48 hours.

In still another embodiment, in the present methods of killing insects, the 7-isopropyl 1,2-dimethyl 3-(4-fluorobenzoyl)indolizine-1,2,7-tricarboxylate (3c) compound can have a high larval mortality rate of 79.08±1.65 in 24 hours and 82.31±2.71 in 48 hours.

In still another embodiment, in the present methods of killing insects, 1-ethyl 7-isopropyl 3-(4-fluorobenzoyl)indolizine-1,7-dicarboxylate (3d) compound can have a high larval mortality rate of 87.32±1.64 in 24 hours and 91.21±3.18 in 48 hours.

In still another embodiment, in the present methods of killing insects, 7-isopropyl 1,2-dimethyl 3-(4-chlorobenzoyl)indolizine-1,2,7-tricarboxylate (3e) compound can have a high larval mortality rate of 67.88±2.91 in 24 hours and 70.91±1.67 in 48 hours.

In still another embodiment, in the present methods of killing insects, 1-ethyl 7-isopropyl 3-(4-chlorobenzoyl)indolizine-1,7-dicarboxylate (3f) compound can have a high larval mortality rate of 65.98±2.94 in 24 hours and 69.19±2.47 in 48 hours.

In still another embodiment, in the present methods of killing insects, 7-isopropyl 1,2-dimethyl 3-(4-bromobenzoyl)indolizine-1,2,7-tricarboxylate (3g) compound can have a high larval mortality rate of 89.41±2.42 in 24 hours and 91.11±2.21 in 48 hours.

In still another embodiment, in the present methods of killing insects, 1-ethyl 7-isopropyl 3-(4-bromobenzoyl)indolizine-1,7-dicarboxylate (3h) compound can have a high larval mortality rate of 82.33±1.23 in 24 hours and 86.66±1.39 in 48 hours.

In still another embodiment, in the present methods of killing insects, 7-isopropyl 1,2-dimethyl 3-(4-cyanobenzoyl)indolizine-1,2,7-tricarboxylate (3i) compound can have a high larval mortality rate of 62.40±1.80 in 24 hours and 63.77±1.90 in 48 hours.

In still another embodiment, in the present methods of killing insects, 1-ethyl 7-isopropyl 3-(4-cyanobenzoyl)indolizine-1,7-dicarboxylate (3j) compound can have a high larval mortality rate of 61.61±1.23 in 24 hours and 66.09±2.62 in 48 hours.

In still another embodiment, in the present methods of killing insects, 7-isopropyl 1,2-dimethyl 3-(4-methylbenzoyl)indolizine-1,2,7-tricarboxylate (3k) compound can have a high larval mortality rate of 57.54±1.32 in 24 hours and 59.98±1.87 in 48 hours.

In still another embodiment, in the present methods of killing insects, 7-isopropyl 1,2-dimethyl 3-(3,5-bis(trifluoromethyl)benzoyl)indolizine-1,2,7-tricarboxylate (3l) compound can have a high larval mortality rate of 97.21±2.30 in 24 hours and 99.52±1.49 in 48 hours.

In still another embodiment, in the present methods of killing insects, 1-ethyl 7-isopropyl 3-(3,5-bis(trifluoromethyl)benzoyl)indolizine-1,7-dicarboxylate (3m) compound can have a high larval mortality rate of 93.45±1.29 in 24 hours and 96.12±1.90 in 48 hours.

In a further embodiment of the present methods, the compounds of formula I can be applied to animal food. More specifically, the compounds of formula I can be applied to cat food. In additional embodiments, the compounds of formula I can be ingested by the larvae of the species *Anopheles arabiensis*.

In an embodiment, the present methods of controlling mosquitos can be effective against mosquitos belonging to a species *Anopheles arabiensis*.

In a further embodiment, the present subject matter relates to a method of making 7-Isopropyl 1-ethyl/methyl 3-(substituted benzoyl)-2-substituted indolizine-1,7-dicarboxylates derivatives of compound I, the method comprising: adding a 1-ethyl/methyl 4-ethyl/methyl but-2-ynedioate 2 molecule to a solution of 1-(2-(substituted phenyl)-2-oxoethyl)-4-(isopropoxycarbonyl)pyridin-1-ium bromides 1 and stirring for at least about 3 hours at about 80° C. Completion of the reaction may be monitored by way of thin layer chromatography. The reaction mixture may be then diluted with ethyl acetate. An organic layer may be separated, washed with brine and dried under sodium sulphate. The crude compound may be purified by column chromatography using hexane and ethyl acetate to afford 76-89% yield of 7-isopropyl 1-ethyl/methyl 3-(substituted benzoyl)-2-substituted indolizine-1,7-dicarboxylates.

The present production methods can be further seen by referring to the following Scheme 1:

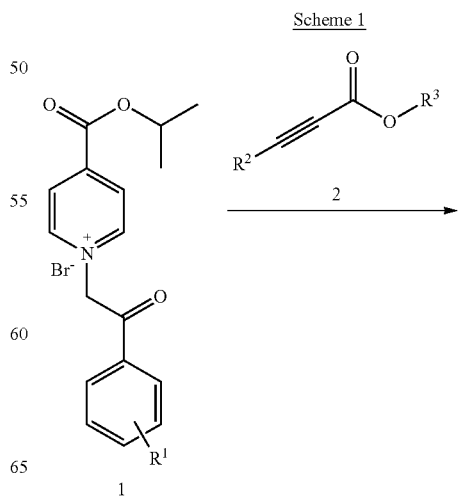

-continued

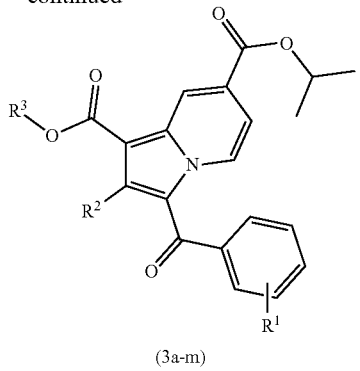

(3a-m)

R[1] = H, CH₃, F, Cl, Br, 3,5-CF₃, CN
R[2] = COOCH₃, COOC₂H₅
R[3] = CH₃, C₂H₅

The following examples relate to various methods of manufacturing certain specific compounds and application results as described herein. All compound numbers expressed herein are with reference to the synthetic pathway figures shown above.

EXAMPLES

The general process for designing of 7-isopropyl 1-ethyl/methyl 3-(substituted benzoyl)-2-substituted indolizine-1,7-dicarboxylates derivatives is a one-pot reaction:

Example 1

General procedure for the preparation of 7-isopropyl 1-ethyl/methyl 3-(substituted benzoyl)-2-substituted indolizine-1,7-dicarboxylates (3a-m)

To a stirred solution of 1-(2-(substituted phenyl)-2-oxoethyl)-4-(isopropoxycarbonyl)pyridin-1-ium bromides 1 (0.002 mol), in water (10 mL), was added 1-ethyl/methyl 4-ethyl/methyl but-2-ynedioate 2 (0.002 mol), stirred at 80° C. for 3h. Completion of the reaction was monitored by way of thin layer chromatography. The reaction mixture was diluted with ethyl acetate. An organic layer was separated, washed with brine and dried under sodium sulphate. The crude compound was purified by column chromatography using hexane and ethyl acetate to afford 76-89% yield of 7-isopropyl 1-ethyl/methyl 3-(substituted benzoyl)-2-substituted indolizine-1,7-dicarboxylates (3a-m).

Example 2

7-Isopropyl 1,2-dimethyl 3-benzoylindolizine-1,2,7-tricarboxylate (3a)

$^1$H NMR (500 MHz, CDCl$_3$) δ 9.56 (d, J=7.4 Hz, 1H), 9.03 (d, J=1.7 Hz, 1H), 7.74-7.72 (m, 2H), 7.65-7.63 (m, 1H), 7.49 (t, J=7.6 Hz, 3H), 5.37-5.32 (m, 1H), 3.94 (d, J=1.1 Hz, 3H), 3.34 (d, J=1.1 Hz, 3H), 1.46 (dd, J=6.3, 1.1 Hz, 6H). $^{13}$C NMR (125 MHz, CDCl$_3$) δ 164.00, 163.02, 132.33, 128.76, 128.26, 127.83, 122.17, 114.88, 69.80, 52.33, 51.95, 21.90.

Example 3

1-Ethyl 7-isopropyl 3-benzoylindolizine-1,7-dicarboxylate (3b)

$^1$H NMR (500 MHz, CDCl$_3$) δ 9.96 (d, J=7.3 Hz, 1H), 9.08 (s, 1H), 7.90 (d, J=1.2 Hz, 1H), 7.87-7.85 (m, 2H), 7.66-7.62 (m, 2H), 7.56 (t, J=7.5 Hz, 2H), 5.38-5.31 (m, 1H), 4.46-4.41 (m, 2H), 1.45 (dd, J=6.1, 1.2 Hz, 9H). $^{13}$C NMR (125 MHz, CDCl$_3$) δ 129.08, 128.53, 114.28, 21.92.

Example 4

7-Isopropyl 1,2-dimethyl 3-(4-fluorobenzoyl)indolizine-1,2,7-tricarboxylate (3c)

$^1$H NMR (500 MHz, CDCl$_3$) δ 9.50 (d, J=7.4 Hz, 1H), 9.03 (d, J=1.8 Hz, 1H), 7.78-7.75 (m, 2H), 7.64 (dt, J=7.4, 1.6 Hz, 1H), 7.17-7.15 (m, 2H), 5.33 (q, J=6.3 Hz, 1H), 3.95 (d, J=1.3 Hz, 3H), 3.44 (d, J=1.3 Hz, 3H), 1.46-1.44 (m, 6H). $^{13}$C NMR (125 MHz, CDCl$_3$) δ 185.38, 164.78, 163.94, 162.96, 136.81, 131.57, 131.42, 131.34, 129.45, 127.77, 122.19, 115.52, 115.34, 114.94, 69.84, 52.47, 52.00, 21.90.

Example 5

1-Ethyl 7-isopropyl 3-(4-fluorobenzoyl)indolizine-1,7-dicarboxylate (3d)

$^1$H NMR (500 MHz, CDCl$_3$) δ 9.92-9.90 (m, 1H), 9.07-9.07 (m, 1H), 7.91-7.89 (m, 2H), 7.87 (s, 1H), 7.65 (dd, J=7.3, 2.0 Hz, 1H), 7.23 (d, J=8.7 Hz, 2H), 5.36-5.31 (m, 1H), 4.45 (q, J=7.1 Hz, 3H), 1.46 (d, J=3.0 Hz, 6H), 1.44 (s, 3H). $^{13}$C NMR (125 MHz, CDCl$_3$) δ 184.39, 166.06, 164.20, 164.05, 163.64, 138.44, 135.60, 135.58, 131.54, 131.47, 129.08, 128.88, 128.47, 123.36, 121.66, 115.78, 115.61, 114.34, 109.08, 69.61, 60.54, 21.91, 14.44.

Example 6

7-Isopropyl 1,2-dimethyl 3-(4-chlorobenzoyl)indolizine-1,2,7-tricarboxylate (3e)

$^1$H NMR (500 MHz, CDCl$_3$) δ 9.54 (d, J=7.4 Hz, 1H), 9.04-9.02 (m, 1H), 7.68-7.66 (m, 2H), 7.48-7.46 (m, 3H), 5.36-5.31 (m, 1H), 3.95 (s, 3H), 3.43 (s, 3H), 1.45 (d, J=6.2 Hz, 6H). $^{13}$C NMR (125 MHz, CDCl$_3$) δ 164.73, 163.91, 162.91, 138.72, 137.44, 136.90, 131.49, 130.17, 129.80, 129.59, 128.81, 128.53, 127.85, 122.16, 121.62, 115.06, 106.82, 69.87, 52.50, 52.01, 21.89.

Example 7

1-Ethyl 7-isopropyl 3-(4-chlorobenzoyl)indolizine-1,7-dicarboxylate (3f)

$^1$H NMR (500 MHz, CDCl$_3$) δ 9.93 (dd, J=7.3, 1.1 Hz, 1H), 9.07 (dd, J=2.0, 1.0 Hz, 1H), 7.86 (s, 1H), 7.83-7.79 (m, 2H), 7.66 (dd, J=7.3, 1.9 Hz, 1H), 7.56-7.53 (m, 2H), 5.37-5.31 (m, 1H), 4.44 (q, J=7.1 Hz, 2H), 1.47-1.43 (m, 9H). $^{13}$C NMR (125 MHz, CDCl$_3$) δ 184.48, 164.17, 163.58, 138.55, 138.28, 137.73, 131.51, 130.45, 129.21, 128.95, 128.85, 128.50, 123.26, 121.64, 114.45, 109.18, 69.64, 60.55, 21.91, 14.44.

Example 8

7-Isopropyl 1,2-dimethyl 3-(4-bromobenzoyl)indolizine-1,2,7-tricarboxylate (3g)

$^1$H NMR (500 MHz, CDCl$_3$) δ 9.55 (d, J=7.4 Hz, 1H), 9.03 (d, J=1.8 Hz, 1H), 8.06 (s, 1H), 7.62 (d, J=10.9 Hz, 4H), 5.34 (s, 1H), 3.95 (s, 3H), 3.43 (s, 3H), 1.45 (d, J=6.2 Hz, 6H): $^{13}$C NMR (126 MHz, CDCl$_3$) δ 185.64, 163.91, 137.88, 131.82, 131.62, 131.50, 130.26, 129.62, 127.87, 127.21, 122.16, 115.08, 69.88, 52.52, 52.02, 21.89.

Example 9

1-Ethyl 7-isopropyl 3-(4-bromobenzoyl)indolizine-1,7-dicarboxylate (3h)

$^1$H NMR (500 MHz, CDCl$_3$) δ 9.93 (d, J=7.3 Hz, 1H), 9.08 (d, J=1.7 Hz, 1H), 7.86 (s, 1H), 7.72 (q, J=8.4 Hz, 4H), 7.69-7.65 (m, 1H), 5.34 (p, J=6.3 Hz, 1H), 4.44 (q, J=7.1 Hz, 2H), 1.47-1.44 (m, 6H); $^{13}$C NMR (126 MHz, CDCl$_3$) δ 184.59, 164.16, 163.57, 138.57, 138.18, 131.82, 131.66, 130.59, 129.24, 128.97, 128.51, 126.77, 123.22, 121.64, 114.48, 109.20, 69.64, 60.55, 21.91, 14.45.

Example 10

7-isopropyl 1,2-dimethyl 3-(4-cyanobenzoyl)indolizine-1,2,7-tricarboxylate (3i)

$^1$H NMR (500 MHz, CDCl$_3$) δ 9.69 (d, J=7.4 Hz, 1H), 9.05 (s, 1H), 8.19 (d, J=8.2 Hz, 1H), 7.79 (s, 4H), 5.39-5.29 (m, 1H), 3.95 (s, 3H), 3.39 (s, 3H), 1.46 (d, J=6.4 Hz, 6H): $^{13}$C NMR (126 MHz, CDCl$_3$) δ 132.28, 131.95, 130.55, 130.24, 129.12, 122.11, 115.59, 70.03, 52.55, 52.12, 21.88.

Example 11

1-Ethyl 7-isopropyl 3-(4-cyanobenzoyl)indolizine-1,7-dicarboxylate (3j)

$^1$H NMR (500 MHz, CDCl$_3$) δ 9.96 (d, J=7.3 Hz, 1H), 9.09 (d, J=1.7 Hz, 1H), 7.94 (d, J=8.0 Hz, 2H), 7.87 (d, J=7.9 Hz, 2H), 7.82 (s, 1H), 7.71 (dd, J=7.3, 1.9 Hz, 1H), 5.42-5.26 (m, 1H), 4.44 (q, J=7.1 Hz, 2H), 1.45 (d, J=6.2 Hz, 6H): $^{13}$C NMR (126 MHz, CDCl$_3$) δ 183.70, 164.02, 163.38, 143.15, 138.91, 132.40, 132.31, 130.59, 129.77, 129.42, 129.26, 128.63, 122.85, 121.66, 118.04, 115.26, 114.88, 109.65, 69.79, 60.68, 21.91, 14.43.

Example 12

7-Isopropyl 1,2-dimethyl 3-(4-methylbenzoyl)indolizine-1,2,7-tricarboxylate (3k)

$^1$H NMR (500 MHz, CDCl$_3$) δ 9.47 (d, J=7.4 Hz, 1H), 9.02 (s, 1H), 7.99 (d, J=7.9 Hz, 1H), 7.72-7.47 (m, 5H), 5.34 (m, 2H), 3.94 (s, 4H), 3.37 (s, 4H), 1.45 (d, J=6.3 Hz, 6H); $^{13}$C NMR (125 MHz, CDCl$_3$) δ 163.09, 143.26, 130.20, 129.18, 129.09, 128.99, 128.94, 127.69, 122.21, 114.67, 69.75, 52.33, 51.92, 21.90, 21.69.

Example 13

7-Isopropyl 1,2-dimethyl 3-(3,5-bis(trifluoromethyl)benzoyl)indolizine-1,2,7-tricarboxylate (3l)

$^1$H NMR (500 MHz, CDCl$_3$) δ 9.69 (d, J=7.4 Hz, 1H), 9.07 (d, J=1.7 Hz, 1H), 8.16 (s, 2H), 8.09 (s, 1H), 7.74 (dd, J=7.4, 1.9 Hz, 1H), 5.43-5.28 (m, 1H), 3.95 (s, 3H), 3.40 (s, 3H), 1.47 (d, J=6.3 Hz, 6H): $^{13}$C NMR (126 MHz, CDCl$_3$) δ 122.13, 70.08, 52.62, 21.88.

Example 14

1-Ethyl 7-isopropyl 3-(3,5-bis(trifluoromethyl)benzoyl)indolizine-1,7-dicarboxylate (3m)

$^1$H NMR (500 MHz, CDCl$_3$) δ 9.95 (d, J=7.3 Hz, 1H), 9.10 (d, J=1.8 Hz, 1H), 8.28 (s, 2H), 8.13 (s, 1H), 7.80 (s, 1H), 7.73 (dd, J=7.4, 1.9 Hz, 1H), 5.35 (m, 1H), 4.45 (q, J=7.1 Hz, 2H), 1.46 (d, J=6.5 Hz, 6H): $^{13}$C NMR (125 MHz, CDCl$_3$) δ 182.18, 163.95, 163.23, 141.29, 139.14, 132.32, 132.05, 130.02, 129.11, 128.90, 128.64, 125.09, 124.01, 122.49, 121.84, 121.67, 115.08, 109.98, 69.85, 60.71, 21.89, 14.35.

Example 15

Larvicidal Screening

*Anopheles arabiensis* was used in the study according to the protocol described by WHO (1975) guidelines in an insectary simulating the temperature (27.5° C.), humidity (70%), and lighting (12/12) of a malaria-endemic environment. One mL of test compound (1 mg/mL) was added to 1 mL of acetone and followed by 249 mL of distilled water to obtain a final concentration of 4 μg/mL. Thirty individuals of 3rd instar larvae were introduced into a container. Negative control was set up using the solvent (acetone) and distilled water, and a positive control included Temephos, which is an active emulsified organophosphate larvicidal used by malaria control programs. Larval mortality was examined for each container separately for 24 h and fed specially made cat food that contained less oil/fat content. The percentage of mortality was determined relative to the initial number of larvae exposed.

Statistical Analysis

Differences in larval mortality between treatments were assessed with generalized linear models using a quasi-Poisson link function. *Anopheles arabiensis* mortality was the dependent variable, while fixed effects were test compounds and observation period (24 and 48 h). A p-value <0.05 was considered statistically significant. Throughout the text, the results are presented as the adjusted mean±the standard error.

The results of the larvicidal screening can be observed in Table 2, below.

TABLE 2
Mortality of *Anopheles arabiensis* larvae exposed for 24 and 48 h to a series of 7-isopropyl 1-ethyl/methyl 3-(substituted benzoyl)-2-substituted indolizine-1,7-dicarboxylates (4 μg/mL) that resulted in high overall larval mortality (>70%). [A-F]. Means with a common letter are not significantly different (p <0.05)
| Compound code | Compound code | Mortality 24 h | 48 h |
|---|---|---|---|
| 3a | 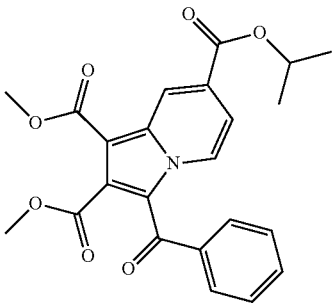 [SMILES: COC(=O)c1c(C(=O)OC)c2cc(C(=O)OC(C)C)ccn2c1C(=O)c1ccccc1] | 39.19 ± 1.64 | 45.53 ± 2.65 |
| 3b | 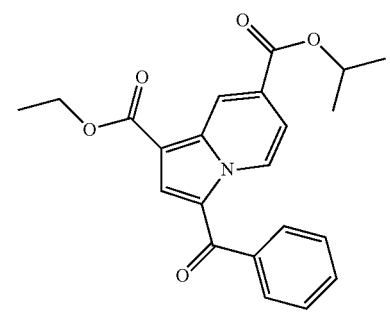 [SMILES: CCOC(=O)c1cc(C(=O)c2ccccc2)n2ccc(C(=O)OC(C)C)cc12] | 32.57 ± 2.44 | 36.76 ± 1.79 |
| 3c | 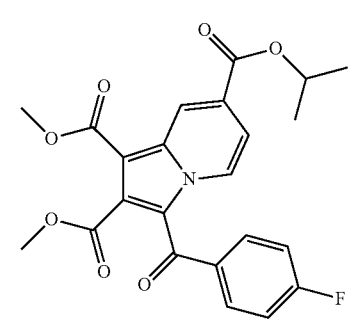 [SMILES: COC(=O)c1c(C(=O)OC)c2cc(C(=O)OC(C)C)ccn2c1C(=O)c1ccc(F)cc1] | 79.08 ± 1.65 | 82.31 ± 2.71 |
| 3d | 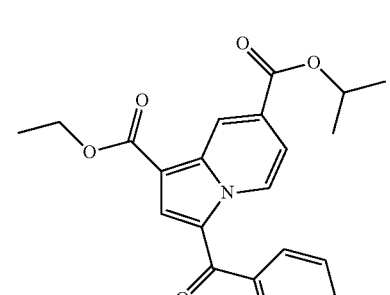 | 87.32 ± 1.64 | 91.21 ± 3.18 |

TABLE 2-continued

Mortality of *Anopheles arabiensis* larvae exposed for 24 and 48 h to a series of 7-isopropyl 1-ethyl/methyl 3-(substituted benzoyl)-2-substituted indolizine-1,7-dicarboxylates (4 μg/mL) that resulted in high overall larval mortality (>70%). [A-F]. Means with a common letter are not significantly different (p <0.05)

| Compound code | Compound code | Mortality | |
|---|---|---|---|
| | | 24 h | 48 h |
| 3e | | 67.88 ± 2.91 | 70.91 ± 1.67 |
| 3f | | 65.98 ± 2.94 | 69.19 ± 2.47 |
| 3g | | 89.41 ± 2.42 | 91.11 ± 2.21 |
| 3h | | 82.33 ± 1.23 | 86.66 ± 1.39 |

TABLE 2-continued

Mortality of *Anopheles arabiensis* larvae exposed for 24 and 48 h to a series of 7-isopropyl 1-ethyl/methyl 3-(substituted benzoyl)-2-substituted indolizine-1,7-dicarboxylates (4 μg/mL) that resulted in high overall larval mortality (>70%). [A-F]. Means with a common letter are not significantly different ($p < 0.05$)

| Compound code | Compound code | Mortality | |
|---|---|---|---|
| | | 24 h | 48 h |
| 3i | | 62.40 ± 1.80 | 63.77 ± 1.90 |
| 3j | | 61.61 ± 1.23 | 66.09 ± 2.62 |
| 3k | | 57.54 ± 1.32 | 59.98 ± 1.87 |
| 3l | | 97.21 ± 2.30 | 99.52 ± 1.49 |

TABLE 2-continued

Mortality of *Anopheles arabiensis* larvae exposed for 24 and 48 h to a series of 7-isopropyl 1-ethyl/methyl 3-(substituted benzoyl)-2-substituted indolizine-1,7-dicarboxylates (4 μg/mL) that resulted in high overall larval mortality (>70%). [A-F]. Means with a common letter are not significantly different (p <0.05)

| Compound code | Compound code | Mortality | |
|---|---|---|---|
| | | 24 h | 48 h |
| 3m | 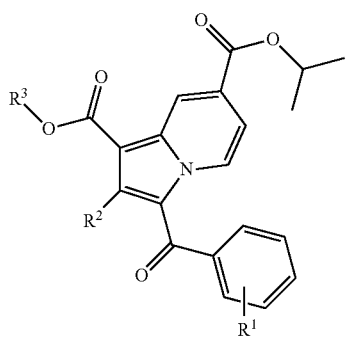 | 93.45 ± 1.29 | 96.12 ± 1.90 |
| Acetone | | 1.99 ± 0.65[N] | 2.09 ± 0.79[B] |
| Temephos | | 98.31 ± 2.4[A] | 100.00 ± 2.65[A] |

It is to be understood that the methods of making and the 7-isopropyl 1-ethyl/methyl 3-(substituted benzoyl)-2-substituted indolizine-1,7-dicarboxylates derivatives, and the use of compositions containing the same, are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

$$I$$

wherein:
$R^1$ is selected from the group consisting of H, $CH_3$, F, Cl, Br, 3,5-$CF_3$, and CN;
$R^2$ is selected from the group consisting of $COOCH_3$ and $COOC_2H_5$; and
$R^3$ is selected from the group consisting of $CH_3$ and $C_2H_5$.

2. The compound of claim 1, wherein $R^1$ is selected from the group consisting of H, $CH_3$, F, Cl, Br, 3,5-$CF_3$, and CN, $R^2$ is $COOCH_3$, and $R^3$ is $CH_3$.

3. The compound of claim 1, wherein $R^1$ is selected from the group consisting of H, $CH_3$, F, Cl, Br, 3,5-$CF_3$, and CN, $R^2$ is $COOC_2H_5$, and $R^3$ is $C_2H_5$.

4. The compound of claim 1, wherein the compound is selected from the group consisting of:
7-isopropyl 1,2-dimethyl 3-benzoylindolizine-1,2,7-tricarboxylate (3a);
7-isopropyl 1,2-dimethyl 3-(4-fluorobenzoyl)indolizine-1,2,7-tricarboxylate (3c);
7-isopropyl 1,2-dimethyl 3-(4-chlorobenzoyl)indolizine-1,2,7-tricarboxylate (3e);
7-isopropyl 1,2-dimethyl 3-(4-bromobenzoyl)indolizine-1,2,7-tricarboxylate (3g);
7-isopropyl 1,2-dimethyl 3-(4-cyanobenzoyl)indolizine-1,2,7-tricarboxylate (3i);
7-isopropyl 1,2-dimethyl 3-(4-methylbenzoyl)indolizine-1,2,7-tricarboxylate (3k); and
7-isopropyl 1,2-dimethyl 3-(3,5-bis(trifluoromethyl)benzoyl)indolizine-1,2,7-tricarboxylate (3l).

5. An insecticidally acceptable composition comprising an insecticidally effective amount of the compound of claim 1 and an insecticidally acceptable carrier.

6. A method of killing larvae, belonging to a species *Anopheles arabiensis*, comprising applying to said larvae or to a target site of insect infestation a larvicidal effective amount of the compound of claim 1.

7. The method of killing larvae of claim 6, wherein the overall larvae mortality rate is greater than 70% after 24 hours.

8. The method of killing larvae of claim 6, wherein the overall larvae mortality rate is greater than 70% after 48 hours.

9. The method of killing larvae of claim 6, wherein the compound is ingested by the larvae.

10. The method of claim 6, wherein the compound is mixed with acetone.

11. The method of killing larvae of claim 6, wherein the compound is applied to cat food.

12. A method of killing insects and larvae comprising applying to said insects and larvae or to a target site of insect infestation a larvicidal effective amount of a larvicidal active compound of the formula I:

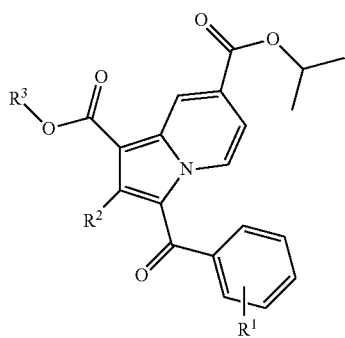

wherein:
$R^1$ is selected from the group consisting of H, $CH_3$, F, Cl, Br, 3,5-$CF_3$, and CN;
$R^2$ is selected from the group consisting of $COOCH_3$ and $COOC_2H_5$; and
$R^3$ is selected from the group consisting of $CH_3$ and $C_2H_5$;
wherein the insects and larvae belong to a species *Anopheles arabiensis*.

13. The method of claim 12, wherein $R^1$ is selected from the group consisting of H, $CH_3$, F, Cl, Br, 3,5-$CF_3$, and CN, $R^2$ is $COOCH_3$, and $R^3$ is $CH_3$.

14. The method of claim 12, wherein the compound is selected from the group consisting of:
    7-isopropyl 1,2-dimethyl 3-benzoylindolizine-1,2,7-tricarboxylate (3a);
    7-isopropyl 1,2-dimethyl 3-(4-fluorobenzoyl)indolizine-1,2,7-tricarboxylate (3c);
    7-isopropyl 1,2-dimethyl 3-(4-chlorobenzoyl)indolizine-1,2,7-tricarboxylate (3e);
    7-isopropyl 1,2-dimethyl 3-(4-bromobenzoyl)indolizine-1,2,7-tricarboxylate (3g);
    7-isopropyl 1,2-dimethyl 3-(4-cyanobenzoyl)indolizine-1,2,7-tricarboxylate (3i);
    7-isopropyl 1,2-dimethyl 3-(4-methylbenzoyl)indolizine-1,2,7-tricarboxylate (3k); and
    7-isopropyl 1,2-dimethyl 3-(3,5-bis(trifluoromethyl)benzoyl)indolizine-1,2,7-tricarboxylate (3l).

15. The method of claim 12, wherein the overall larvae mortality rate is greater than 70% after 24 hours or 48 hours.

16. The method of claim 12, wherein the compound is mixed with acetone.

17. The method of claim 12, wherein the compound is ingested by a larvae.

* * * * *